United States Patent [19]

Douglas

[11] 4,195,624
[45] Apr. 1, 1980

[54] TUBULAR SHEATH FOR FACILITATING THE INSERTION OF AN ENDOSCOPE

[76] Inventor: Donald D. Douglas, 708 Highland Ter., Williamsport, Pa. 17701

[21] Appl. No.: 914,164

[22] Filed: Jun. 9, 1978

[51] Int. Cl.$^2$ .................... A61B 1/06; A61M 25/00
[52] U.S. Cl. ................................. 128/8; 128/772
[58] Field of Search ............... 128/4, 5, 6, 7, 8, 348, 128/349 B, 349 R, 349 BV, 351, 214.4, 2 M, 341, DIG. 9, DIG. 16, 350 R, 350 V, 239, 240; 254/134.3 FT; 15/104.3 SN

[56] References Cited

U.S. PATENT DOCUMENTS

| | | | |
|---|---|---|---|
| 243,396 | 6/1881 | Pfarre | 128/349 R |
| 1,045,326 | 11/1912 | Ruflin | 128/240 |
| 1,704,764 | 3/1929 | Schellberg | 128/6 |
| 1,710,701 | 4/1929 | Hertzberg | 128/348 |
| 2,118,631 | 5/1938 | Wappler | 128/DIG. 9 |
| 2,139,653 | 12/1938 | Belfrage | 128/251 |
| 2,243,992 | 6/1941 | Wappler | 128/8 |
| 2,268,321 | 12/1941 | Flynn | 128/349 R |
| 2,657,691 | 11/1953 | Nordstrom | 128/303 R |
| 3,114,373 | 12/1963 | Andersen | 128/350 R |
| 3,858,577 | 1/1975 | Bass et al. | 128/8 |
| 4,146,019 | 3/1979 | Bass et al. | 128/6 |

FOREIGN PATENT DOCUMENTS

| | | | |
|---|---|---|---|
| 201289 | 1/1908 | Fed. Rep. of Germany | 128/7 |
| 1211360 | 2/1966 | Fed. Rep. of Germany | 128/6 |
| 286682 | 10/1952 | Switzerland | 128/251 |

Primary Examiner—Robert W. Michell
Assistant Examiner—Arthur S. Rose
Attorney, Agent, or Firm—Hill, Van Santen, Steadman, Chiara & Simpson

[57] ABSTRACT

A device for facilitating insertion of an endoscope into the esophagus which includes an elongated tube composed of a flexible elastomer, the tube having a substantially uniform outer diameter along most of its length and a solid tapered tip end, the tip end being joined to the remainder of the tube by means of a hollow tapered neck portion. The tube is provided with an opening behind the neck of generally elongated configuration. The geometry of the opening and the flexibility of the tube are such that when the distal end of an endoscope is inserted into the aperture, the distal end is slightly bent and is received in wedged engagement within the tapered neck portion, and a portion immediately behind the distal end of the endoscope is resiliently supported by a portion of the periphery of the opening formed in the tube.

5 Claims, 6 Drawing Figures

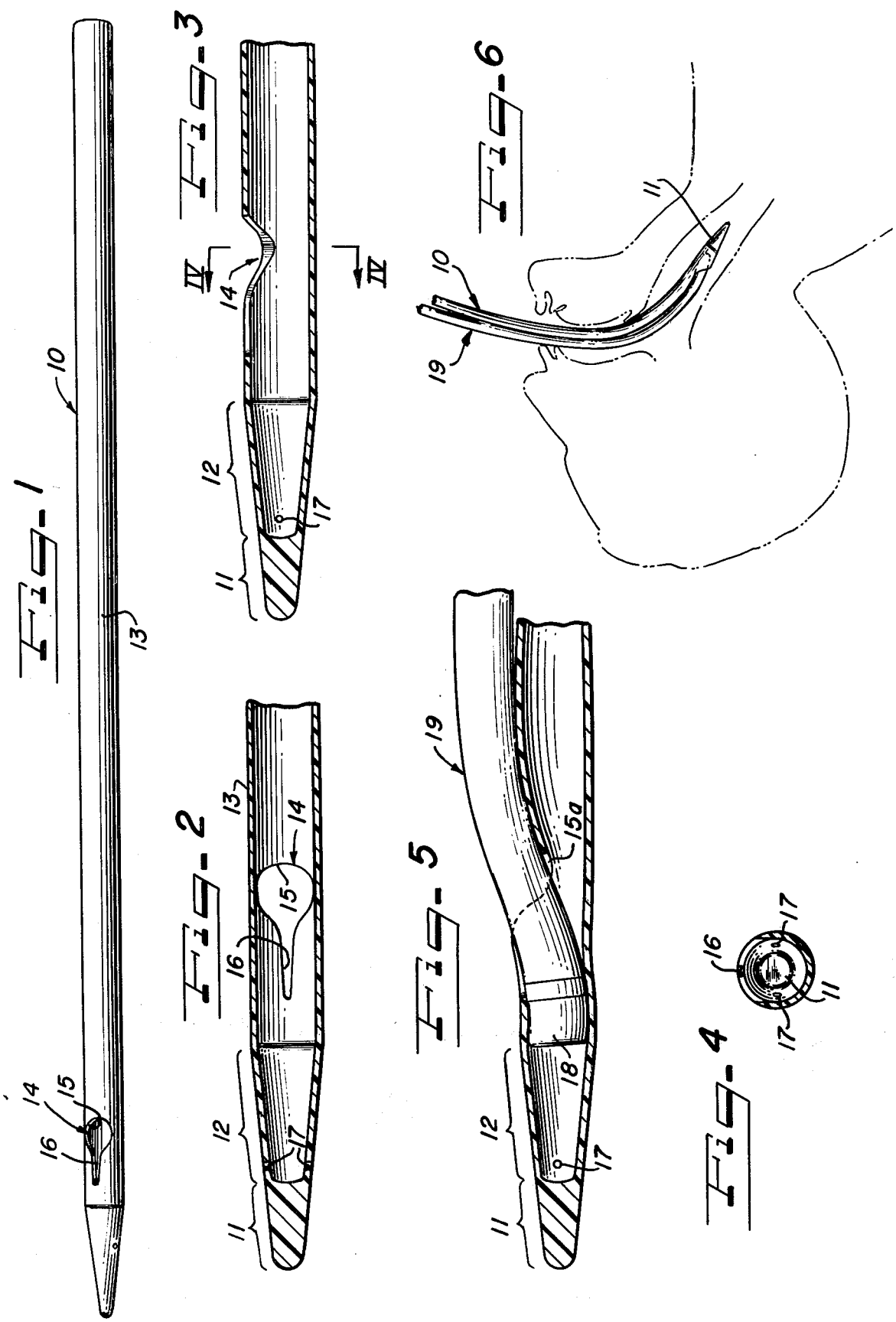

TUBULAR SHEATH FOR FACILITATING THE INSERTION OF AN ENDOSCOPE

BACKGROUND OF THE INVENTION

1. Field of the Invention

This invention is in the field of medical devices and, in particular, to devices which facilitate the insertion of an endoscope into the esophagus, and is arranged to be withdrawn from the esophagus when the endoscope is in proper position.

2. Description of the Prior Art

Endoscopy is a major contributor to effective diagnosis and treatment of various gastrointestinal disorders. There are, however, numerous patients with normal upper esophageal anatomy into which the endoscope cannot be passed. This inability severely limits the help which might otherwise be provided for the patient.

Turning to the patented art, the Wappler U.S. Pat. No. 2,243,992 describes an operating instrument of the endoscopic type which includes a flexible telescope tube and a flexible operating tube in side-by-side relationship with means retaining the tubes together as a flexible unit. The operating tube has an outlet end adjacent to the objective of the telescope, and an illuminating means is provided in the forward end of the instrument for illuminating the operating field which is viewed by the objective. Both the telescope and the operating tubes have rearward portions that are relatively rigid and forward portions of flexible construction. A relatively rigid shell is provided at the forward end of the instrument, and is secured to both flexible tubes at their forward ends. The flexible portions of the tubes are preferably composed of helically wound material such as spring metal or the like.

Hett, U.S. Pat. No. 2,519,760 is merely of general interest in that it describes a gastroscope which has a rigid forward portion, a flexible intermediate portion, and a rigid rearward portion.

Ferris et al U.S. Pat. No. 3,057,345 describes an endoscope for distending a body cavity by inflating it with air. The endoscope has two separate longitudinal air passageways. The first passageway extends down to the tip of the endoscope and communicates with the interior of an inflatable bulb. The second passageway terminates near the front end of the endoscope and opens exteriorly thereof. Air may be forced through this second passageway. In operation, the first mentioned inflatable bulb may be inflated so as to block off the duodenal cap from the remaining portion of the duodenum, and the second passageway is filled with air to inflate the duodenal cap after the lower end has been stopped by the inflatable bulb.

Bass et al U.S. Pat. No. 3,858,577 describes a flexible endoscope with a laser connected therein for simultaneous viewing and performance of surgery on the interior stomach wall. A low power laser operates in the visible light range with the laser beam directed to one or more individual fiber optic fibers carried on the endoscope for performing laser surgery.

Harautuneian U.S. Pat. No. 3,862,635 describes an endotracheal tube which includes a preformed inflatable plastisol balloon telescopically fitted over and secured to a forward end portion of a dual-lumen tube.

Mori U.S. Pat. No. 3,888,237 describes an endoscope which has a channel therein, and provided with a device to measure the pH of an abdominal liquid, the device including a glass electrode, a thin flexible tube fitted at one end to the electrode to bring the electrode to the liquid whose pH is to be measured, and a lead having one end connected to the glass electrode and the opposite end extending through the flexible tube to the outside.

Kawahara U.S. Pat. No. 3,913,565 recognizes the difficulty in inserting an intestinal tube into the patient's body. The subject of this patent is a guide tube which includes an elongated, flexible main body having an inner diameter sufficient to accept an endoscope, or other body cavity treating instrument. A balloon is attached to the main body in proximity to the forward end thereof, which balloon is expanded by air or liquid fed thereto. A flexible tube section extends forwardly from the balloon and is integral with the forward end of the main body but possesses more flexibility than the main body.

Hosono U.S. Pat. No. 3,948,251 describes a flexible tube endoscope comprising an outer flexible tube member, a central tube member formed by coiling a strip member and disposed within the outer flexible member along the longitudinal direction thereof, and an operating section connected to one end of the central tube member and operated by means of a control unit to vary the pliability of the flexible tube by varying the diameter of the central tube member.

SUMMARY OF THE INVENTION

This invention provides a device for facilitating insertion of an endoscope into the esophagus. It consists of an elongated tube composed of a flexible elastomer, the tube having a substantially uniform outer diameter along most of its length, and a solid tapered tip end. A hollow tapered neck portion joins the solid tapered tip end to the remainder of the tube. The tube is also provided with an opening behind the neck of generally elongated configuration, the opening being sufficiently large to receive the distal end of an endoscope therethrough. In passing through the opening, the endoscope is slightly bent and is received in wedged engagement within the neck portion of the tube. The geometry of the tube and its material of construction is such that resilient support is provided for a portion of the endoscope near the distal end thereof when the distal end is received within the tapered neck portion. The tube thereby serves to facilitate insertion of the endoscope into the esophagus, and is readily removed from the endoscope by a relatively simple twisting movement, whereupon the tube can be removed leaving the endoscope properly positioned for use.

BRIEF DESCRIPTION OF THE DRAWINGS

A preferred embodiment of the present invention has been illustrated in the drawings, in which:

FIG. 1 is a plan view of the tube;

FIG. 2 is a fragmentary cross sectional view on an enlarged scale illustrating the distal portion of the tube;

FIG. 3 is a view similar to FIG. 2, but rotated 90° from FIG. 2;

FIG. 4 is a cross sectional view taken substantially along the line IV—IV of FIG. 3;

FIG. 5 is a fragmentary view in cross section illustrating the manner in which the distal end of the endoscope is received within the protective tube; and FIG. 6 is a relatively schematic view showing how the tube and endoscope are jointly received through the oral cavity of the patient and into the esophagus.

DESCRIPTION OF THE PREFERRED EMBODIMENTS

In FIG. 1, reference numeral 10 has been applied generally to a flexible tube according to the present invention. The tube 10 is generally about 23 inches (58.4 cm) in length and is composed of a flexible elastomer, such as a silicone rubber. I particularly prefer at this time to use a flexible elastomer known as "D4" manufactured by the Dureco Company of Boston, Massachusetts because it has the proper flexibility and is optically transparent. Whatever material is used, it should provide flexibility but sufficient strength to pass the endoscope past the upper esophageal sphincter.

As best seen in FIGS. 2 to 4, the tube 10 has a tapered solid end portion 11 and a hollow tapered neck portion 12 which connects the tip portion 11 to a relatively uniform diameter tubular portion 13.

Immediately behind the tapered neck portion 12 is an aperture 14 of elongated teardrop configuration including a generally circular portion 15 terminating in a relatively narrow slot 16 having a width of about 1 mm and extending parallel to the axis of the tube 10. The neck portion 12 is also provided with a pair of apertures 17 which serve as a venting means for removing air which is compressed within the neck portion 12 as the distal end of the endoscope is received therein, and to prevent or minimize suction retention of the endoscope in the tube 10 at the time when separation is intended to occur.

As best seen in FIG. 5 a distal end portion 18 of an endoscope 19 is proportioned to be received within the circular portion 15 of the opening 14, and to be held therein in releasable wedged engagement along the walls of the tapered neck portion 12. As shown in FIG. 5, the distal portion 18 undergoes a slight bending from its normal position in being received through the opening 14. The flexible distal portion 18 thereby provides a slight bias against the tapered neck portion 12. An additional biasing in the same direction is provided by a wall portion 15a which forms part of the periphery of the circular portion 15. The material of the tube 10 is sufficiently strong so that the tube does not collapse due to the weight of the endoscope but is held supported as illustrated in FIG. 5.

Typically, the tube 10 will have an outer diameter of between 16 and 17 mm, and an inner diameter of about 13 and 14 mm. Thus, the size of the device is no larger than conventional dilators which can be easily passed in patients with normal upper esophageal sphincters.

Prior to insertion of the endoscope head 18, the interior of the neck portion 12 and the opening 14 are lubricated with a suitable lubricant such as a liquid silicone oil. The distal end portion 18 of the endoscope is then inserted through the opening 14 and into engagement with the tapering walls of the neck portion 12. The endoscope can, of course, also be lubricated with a suitable gel. The tube 10 with the endoscope in place, as shown in FIG. 6 is then passed in the usual manner after the patient has had standard pre-medication and oral anesthesia. The flexible tip 11 of the tube readily passes through the upper esophageal sphincter, usually without the necessity of having the patient actively swallow. The tube 10 with the endoscope 19 contained therein is then inserted to a depth of 25 to 30 cm, measured on the side of the endoscope 19. This puts the endoscope in position for proper viewing. The tube 10 is then held stationary with one hand, while the other hand pulls the endoscope 19 back a few centimeters. The distal end 18 of the endoscope easily slips out of the opening 19. After the endoscope has been disengaged from the tube, the tube is advanced slightly and simultaneously turned counterclockwise about ¼ of a turn. The tube 10 is then removed from the patient and the endoscope 19 is held stationary, leaving it in the esophagus. There is little discomfort, if any, to the patient in this maneuver in that the tube is soft and pliable and conforms to the contour of the endoscope. The tube 10 flattens somewhat along the ventral portion of the upper esophagus and hypopharynx.

When the endoscope is withdrawn a few centimeters, the distal portion of the tube is kept in place by the esophageal walls and due to its length, the tube does not fold back on itself. Since it is made of a soft pliable material, it will not traumatize the esophagus. As the endoscope is withdrawn and has cleared the front edge of the opening 14, there is a natural tendency for the endoscope, due to its resiliency, to return to a straight position. This, coupled with the resiliency at the wall portion 15a tends to return the endoscope distal end to its natural position. Thus, the head of the endoscope looks directly down the esophagus.

The device of the present invention can be used for all endoscopies where there is no contra-indication. Patients who exhibit spasm of the upper esophageal sphincter or cervical spurs could be examined more readily through the use of the device of the present invention. In uncooperative patients who need endoscopy, the patient can be more deeply sedated and endoscopy carried out because the device does not depend upon the patient swallowing as in normal endoscopy. Anesthetized patients in the operating room or on ventilators can be more easily examined using the device of the present invention.

The device of the present invention is not intended for use in patients with abnormal upper esophageal anatomy.

It should be evident that various modifications can be made to the described embodiments without departing from the scope of the present invention.

I claim as my invention:

1. In a protective device for assembly with an endoscope and for insertion of the thus assembled elements into an esophagus, the protective device comprising an elongated tube composed of a flexible elastomer and having an outside diameter not exceeding 17 mm., said tube having a substantially uniform outer diameter along most of its length and a solid tapered tip end, a hollow tapered neck portion extending from said tip end to the portion of uniform diameter, said tube being provided with a tear shaped opening behind said neck portion of generally elongated configuration, said tear shaped opening being sufficiently large to receive the distal end of an endoscope therethrough, said opening being configured so as to provide resilient support for a portion of an endoscope near the distal end when the distal end is received in said tapered neck portion, the wall defining the tear shaped opening at the area most remote from the solid tapered tip and being resiliently collapsible to facilitate insertion of the forward end of an endoscope through the tear shaped opening and into the tube so that an endoscope can engage interiorly of the tube with its side wall with a forward end of the endoscope being disposed in close proximity to said solid tapered tip end of the tube, said tube having means in said tapered neck portion to provide for bleed-off of air when said endoscope is being inserted into said tapered neck portion, said tear shaped opening having a generally circular portion terminating in a relatively narrow elongated slot parallel to the axis of the tube, said slot having a length greater than and a width less than the diameter of the circular portion, said tear shaped opening having its narrowest end in closest proximity to said solid tapered tip end.

2. In combination, a protective device and an endoscope in assembly together for insertion into an esophagus, the endoscope comprising a first flexible elongated tube having a distal end and a proximal end, the protective device comprising a second elongated tube composed of a flexible elastomer and having an outside diameter not exceeding 17 mm., said second tube having a substantially uniform outer diameter along most of its length and a solid tapered tip end, a hollow tapered neck portion extending from said tip end to the portion of uniform diameter, said neck portion having an inner diameter that varies from a diameter less than the diameter of the distal end of the first tube at a point in the neck portion adjacent the solid tip to a diameter greater than the distal end of the first tube at a point in the neck portion adjacent the portion of uniform diameter, said second tube being provided with a tear shaped opening behind said neck portion of generally elongated configuration, said tear shaped opening being configured so as to provide resilient support for a portion of said endoscope near said distal end when said distal end is received in said tapered neck portion, said distal end of said first tube being received through said tear shaped opening and in wedged engagement with the interior of the tapered neck portion, said second tube having means in said tapered neck portion to provide for admitting air to relieve suction when said first tube is removed from said tapered neck portion.

3. The combination of claim 2 in which said tapered neck portion includes a plurality of spaced apertures permitting air to be vented from said tapered neck portion.

4. The combination of claim 2 in which said distal end of said first tube is bent as a result of being received in said wedged engagement.

5. In a protective device for assembly with an endoscope and for insertion of the thus assembled elements into an esophagus, the protective device comprising an elongated tube composed of a flexible elastomer and having an outside diameter not exceeding 17 mm., said tube having a substantially uniform outer diameter along most of its length and a solid tapered tip end, a hollow tapered neck portion extending from said tip end to the portion of uniform diameter, said tube being provided with a tear shaped opening behind said neck portion of generally elongated configuration, said tear shaped opening being sufficiently large to receive the distal end of an endoscope therethrough, said opening being configured so as to provide resilient support for a portion of an endoscope near the distal end when the distal end is received in said tapered neck portion, the wall defining the tear shaped opening at the area most remote from the solid tapered tip end being resiliently collapsible to facilitate insertion of the forward end of an endoscope through the tear shaped opening and into the tube so that an endoscope can engage interiorly of the tube with its side wall with a forward end of the endoscope being disposed in close proximity to said solid tapered tip end of the tube, said tube having means in said tapered neck portion to provide for bleed-off of air when said endoscope is being inserted into said tapered neck portion, said tear shaped opening having a generally circular portion terminating in a relatively narrow elongated slot parallel to the axis of the tube, said slot having a length greater than and a width less than the diameter of the circular portion.

* * * * *